(12) United States Patent
Attinger

(10) Patent No.: US 11,678,792 B2
(45) Date of Patent: Jun. 20, 2023

(54) ENDOSCOPIC DEVICE

(71) Applicant: KARL STORZ SE & Co. KG, Tuttlingen (DE)

(72) Inventor: Jürg Attinger, Stein am Rhein (CH)

(73) Assignee: KARL STORZ SE & Co. KG, Tuttlingen (DE)

( * ) Notice: Subject to any disclaimer, the term of this patent is extended or adjusted under 35 U.S.C. 154(b) by 352 days.

(21) Appl. No.: 16/844,644

(22) Filed: Apr. 9, 2020

(65) Prior Publication Data

US 2020/0345208 A1    Nov. 5, 2020

(30) Foreign Application Priority Data

May 2, 2019    (DE) ..................... 10 2019 111 347.4

(51) Int. Cl.
*A61B 1/005*    (2006.01)
*A61B 1/00*    (2006.01)
*A61M 16/04*    (2006.01)

(52) U.S. Cl.
CPC .......... *A61B 1/0055* (2013.01); *A61B 1/0014* (2013.01); *A61B 1/00128* (2013.01); *A61M 16/0463* (2013.01)

(58) Field of Classification Search
CPC ........................ A61B 1/00128; A61B 1/0014
See application file for complete search history.

(56) References Cited

U.S. PATENT DOCUMENTS

| | | | | |
|---|---|---|---|---|
| 5,906,594 A | * | 5/1999 | Scarfone | A61M 25/06 604/165.01 |
| 5,974,904 A | * | 11/1999 | Dirschbacher | F16H 25/24 74/89.32 |
| 6,464,632 B1 | * | 10/2002 | Taylor | A61B 1/005 138/174 |
| 6,881,186 B2 | * | 4/2005 | Smith | A61B 1/015 600/104 |
| 10,149,605 B2 | | 12/2018 | Petersen et al. | |
| 2005/0049459 A1 | * | 3/2005 | Hern | A61B 1/00094 600/121 |
| 2007/0100201 A1 | | 5/2007 | Komiya et al. | |
| 2011/0230878 A1 | * | 9/2011 | Ryan | A61B 17/00234 606/41 |
| 2014/0257253 A1 | * | 9/2014 | Jemison | A61B 1/00133 606/1 |

FOREIGN PATENT DOCUMENTS

JP    2002172118 A    6/2002

* cited by examiner

*Primary Examiner* — Matthew J Kasztejna
(74) *Attorney, Agent, or Firm* — Jason H. Vick; Sheridan Ross, PC

(57) ABSTRACT

The present application is directed to an endoscopic device, including at least one flexible endo scope shaft and at least one kink protector, which is associated with the endoscope shaft and includes at least one base body that has a conical and/or cylindrical design, at least in sections, and that has a main extension direction and a main extension along the main extension direction, and the kink protector includes at least one quick-release coupling, which is configured for a selective connection to a tube and includes at least one fin situated at least substantially perpendicularly on the base body. It is provided that the fin has an extension extending along the main extension direction of the base body at least across 50% of the main extension of the base body.

21 Claims, 6 Drawing Sheets

ENDOSCOPIC DEVICE

CROSS-REFERENCE TO RELATED APPLICATIONS

This application claims the benefit under 35 U.S.C. 119(a) to German Patent Application No. 10 2019 111 347.4, filed May 2, 2019, the disclosure of which is incorporated herein by reference in its entirety.

TECHNICAL FIELD

The invention relates to an endoscopic device and more particularly relates to a shaft thereof.

BACKGROUND OF THE INVENTION

An endoscopic device comprising a flexible endoscope shaft and at least one kink protector associated with the endoscope shaft is already known from U.S. Pat. No. 10,149,605 B2. The kink protector comprises a cylindrical base body and, for selectively connecting the kink protector to a tube, at least one quick-release coupling, which comprises multiple annular ribs that are arranged concentrically and offset from one another along a cylinder axis of the base body and extend at least substantially perpendicularly out of the base body.

In particular, it is the object of the invention to provide a device of the type in question having improved properties with respect to safety. The object is achieved according to the invention by the features of claim 1, whereas advantageous embodiments and further developments of the invention can be derived from the dependent claims.

SUMMARY OF THE INVENTION

The invention is directed to an endoscopic device, comprising at least one flexible endoscope shaft and at least one kink protector associated with the endoscope shaft, which is configured to selectively connect the kink protector to a tube and which comprises at least one base body that has a conical and/or cylindrical design, at least in sections, and that has main extension direction and a main extension along the main extension direction, and the kink protector, for connecting the tube, comprises at least one quick-release coupling, which includes at least one fin situated at least substantially perpendicularly on the base body.

It is provided that the fin has an extension that extends along the main extension direction of the base body across at least 50%, in particular across at least 60%, preferably across at least 70%, and particularly preferred across at least 80% of the main extension of the base body.

In this way, retention of the tube at the kink protector can advantageously be improved, whereby inadvertent detachment can be avoided, and safety can be increased. More advantageously, it is possible to enhance safety during removal of the tube since the kink protector, due to the present design, does not suddenly lose the clamping force thereof, but can be detached evenly and slowly. Further advantageously, the quick-release coupling also achieves a secure connection to tubes that have different inside diameters, for example due to manufacturing tolerances.

An "endoscopic device" shall, in particular, be understood to mean a preferably functioning component part, in particular a subassembly and/or a design component and/or a functional component of an endoscope. The endoscopic device can preferably form the endoscope at least partially, preferably at least to a large degree, and particularly preferred completely. The endoscopic device is, approximately, configured to be inserted at least partially, and preferably at least to a large degree, into an, in particular artificial and/or natural cavity, in particular a body cavity, and more particularly, so as to examine the same. The endoscopic device can be a medical and/or industrial endoscopic device. The term "configured" shall, in particular, be understood as specially programmed, designed, devised, and/or equipped. A component being configured for a particular function shall, in particular, be understood to mean that the component fulfills and/or carries out this particular function in at least one application and/or operating state. An "endoscope shaft" shall, in particular, be understood to mean an elongated part of an endoscope, which is, approximately, designed to be inserted into an, in particular artificial and/or natural cavity, in particular a body cavity. An "elongated part" shall, in particular, be understood to mean a component having a main extension that is greater at least by a factor of five, preferably at least by a factor of ten, and particularly preferred at least by a factor of twenty, than a largest extension of the component perpendicularly to the main extension thereof, that is, in particular, a diameter of the component. A "main extension" of a component shall, in particular, be understood to mean the longest extension thereof along the main extension direction thereof. A "main extension direction" of a component shall, in particular, be understood to mean a direction that extends parallel to a longest edge of a smallest imaginary cuboid, which just barely still completely encloses the component, and that preferably extends through a geometric center and/or through a center of gravity of the component. In particular, the endoscope shaft comprises a distal end section and a proximal end section. An "end section" of a component shall, in particular, be understood to mean a section that, proceeding from one end of the component toward the center of the component, extends no more than 10 cm, preferably no more than 5 cm, and particularly preferably no more than 3 cm. A "distal end section" of a component shall, in particular, be understood to mean an end section that, proceeding from a distal end of the component, extends in a proximal direction. A "proximal end section" of a component shall, in particular, be understood to mean an end section that, proceeding from a proximal end of the component, extends in a distal direction. "Distal" shall, in particular during an operation, be understood to mean facing a patient and/or facing away from an operator. In particular, proximal is the opposite of distal. "Proximal" shall, in particular during an operation, be understood to mean facing away from a patient and/or facing an operator. Further, the endoscopic device, in particular, comprises at least one handle. The handle is, approximately, arranged at the proximal end section of the endoscope shaft. The handle is, in particular, designed for a manual operation of the endoscopic device. The handle comprises, approximately, at least one grip and/or at least one operating element, such as a switch, a button or the like, which is preferably arranged at the grip. A "kink protector" shall, in particular, be understood to mean a component that is configured to avoid sharp twisting of the endoscope shaft, and more particularly at the proximal end section of the endoscope shaft, preferably in the transition region of the endoscope shaft to the handle. Viewed as a whole, the kink protector is, in particular, free of rotational symmetry. The kink protector preferably has mirror symmetry, wherein a mirror plane of the mirror symmetry corresponds to at least one main extension plane of a fin. A "main extension plane" of a component shall, in particular, be understood to mean a plane that is parallel to a largest lateral surface of a smallest imaginary cuboid, which just barely still completely encloses the component, and that, in particular, extends through the center of the cuboid. The tube is, in particular, a breathing tube or an endotracheal tube, which is configured to be inserted into a trachea. The tube includes, in particular, a channel, which is configured to accommodate the endoscope shaft. A "quick-release coupling" shall, in particular, be understood to mean a component that is configured to detachably connect at least two components to one another in a tool-less manner. The quick-release coupling is preferably provided to create a force-fit and/or form-locked connection, such as a clamping connection. "At least substantially perpendicular" shall, in particular, be understood to mean an orientation of a direction relative to a reference direction, in particular in a plane, wherein the direction and the reference direction include an angle of 90°, in particular taking into consideration a maximum deviation of less than 8°, advantageously of less than 5°, and particularly advantageous of less than 2°.

It would be conceivable for the fin to wind around the base body in a thread-like manner. However, so as to achieve, in particular, that the tube can be pulled off safely and smoothly, it is provided that a main extension plane of the fin is oriented at least substantially parallel to the main extension direction of the base body. "At least substantially parallel" shall, in particular, be understood to mean an orientation of a direction relative to a reference direction, in particular in a plane, wherein the direction and the reference direction include an angle of 0°, in particular taking into consideration a maximum deviation of less than 8°, advantageously of less than 5°, and particularly advantageous of less than 2°.

It is furthermore provided that the fin includes at least one outside edge facing away from the base body, wherein an angle of the outside edge relative to the main extension direction decreases along the main extension of the base body, in particular in the proximal direction. Advantageously, safety can be further enhanced since a tube can be centered along the fin during an insertion process. More advantageously, a smooth connection of a tube to the kink protector can be achieved. The angle can decrease continuously and/or incrementally. In particular, the fin comprises different sections in which the angle decreases incrementally. In particular, the angle is no more than 80° in a first section of the fin, no more than 10° in at least a second section of the fin and/or no more than 5° in at least a third section of the fin.

It is provided that the fin is configured to bend laterally upon contact, in particular with the tube. Safety can advantageously be further enhanced. In particular, it is possible to achieve advantageous clamping of a tube at the kink protector. The fin being configured to bend laterally shall, in particular, be understood to mean that the fin, as seen relative to the main extension plane thereof, deforms convexly and/or concavely out of the same.

It is provided that the fin has a maximal height relative to the base body, which corresponds at least to twice a thickness of the fin. Safety can advantageously be further enhanced. In particular, a particularly easy deflection of the fin can be achieved. The thickness is measured, in particular, perpendicular to the main extension plane of the fin.

It is provided that the fin is designed to be at least partially, preferably at least to a large degree, and particularly preferred completely elastic. Advantageously, safety during an installation and/or a removal of the tube can be further enhanced. An "elastic component" shall, in particular, be understood to mean a component that, during a deformation out of a basic position, strives to return to the basic position on its own.

It is further provided that the fin is at least partially, preferably at least to a large degree, and particularly preferably completely made of a material that has a Shore hardness value of at least 40, in particular at least 50, preferably at least 60, and/or of no more than 90, in particular no more than 80, preferably no more than 70. In this way, safety can advantageously be further enhanced. In particular, a good compromise may thus be found between easy installation and/or removal and secure retention of the tube at the kink protector. The expression "at least to a large degree" shall, in particular, be understood to mean at least 55%, preferably at least 65%, preferably at least 75%, particularly preferred at least 85%, and most particularly preferred at least 95%, and advantageously completely, and more particularly with respect to a volume and/or a mass of the component. Particularly preferred, the Shore hardness value is at least substantially 65. "At least substantially" shall, in particular, be understood to encompass a maximum deviation of no more than 10%, preferably of no more than 5%, and particularly preferred of no more than 2%.

It is furthermore provided that the fin is at least partially, preferably at least to a large degree, and particularly preferred completely made of a material, in particular the aforementioned material, which is a thermoplastic elastomer. In particular, safety can be further enhanced. The thermoplastic elastomer is preferably the thermoplastic elastomer known under the trade name Mediprene.

It is furthermore provided that the base body comprises at least one conical section and at least one cylindrical section. In particular, safety can be further enhanced. In particular, a clamping action of the fin between the tube and the base body can advantageously be improved. In particular, the base body can comprise at least two cylindrical sections, which are preferably connected to one another by at least one conical section.

The base body comprises at least one section, in particular a cylindrical section, in which the base body, cut perpendicularly to the main extension direction thereof, has at least a circular ring-shaped cross-section. So as to enable, in particular, secure retention and clearly define an orientation of the tube relative to the kink protector, it is provided that the base body, cut perpendicularly to the main extension direction thereof, has a cross-section deviating from a circular ring shape at least in sections. In particular, at least one conical section of the base body, cut perpendicularly to the main extension direction thereof, has at least a cross-section deviating from a circular ring shape. In the conical section, the base body, cut perpendicularly to the main extension direction thereof, preferably has at least an oval ring-shaped cross-section. The base body is preferably free of rotational symmetry. It is conceivable that individual sections, such as a conical section and/or a circular ring-shaped section, have rotational symmetry, but that these are arranged offset from one another along the respective rotational symmetry axes thereof, so that the base body comprising the sections overall is free of rotational symmetry. As an alternative, the base body could have finite rotational symmetry. The base body preferably has n-fold rotational symmetry, wherein n is a number different from infinite. Particularly preferred, n is an even number and, most particularly preferred, has the value of two.

It is provided that the fin is designed in one piece with the base body. In this way, safety can be further enhanced. In particular, it can be avoided that isolated fins detach from the base body during use and could result in an inadvertent cancellation of the connection of the tube to the kink protector. "In one piece" shall, in particular, be understood to mean at least integrally joined, for example by way of a welding process, an adhesive bonding process, a molding process and/or another process that appears useful to the person skilled in the art, and/or advantageously formed as one piece, such as by production from casting and/or by production in a one-component or multi-component injection molding process, and advantageously from a single blank.

It is provided that the quick-release coupling comprises at least one further fin, which is designed substantially identically to the fin. In this way, safety can advantageously be further enhanced. More advantageously, a clamping force can be increased. The fin and the further fin are, in particular, arranged at a distance from one another in the circumferential direction around the base body. In particular, the quick-release coupling comprises a number of m fins, wherein, in particular, m=n+1 is to apply, and thus is preferably an odd number. The value of the number m is, particularly preferred, three.

It is provided the fin and the further fin are arranged rotationally symmetrically relative to one another about a rotational symmetry axis at the base body. In this way, safety can advantageously be further increased. More advantageously, a symmetrical arrangement of the tube about the kink protector can be achieved, whereby, in particular, mounting the tube on the kink protector can be made safer. In particular, a uniform distribution of clamping forces can be achieved by this arrangement. In particular, the rotational symmetry has the value 1, which is preferably different from the value n, and most particularly preferred is equal to the value m. In particular, a rotational symmetry axis of the annular section of the base body corresponds to the rotational symmetry axis of the fins.

It is provided that the rotational symmetry axis of the fins is different from a main extension direction of the base body. In this way, safety can advantageously be further enhanced. More advantageously, an orientation of the kink protector relative to the tube can be established, whereby a poka-yoke-like association can be achieved. In particular, a rotational symmetry axis about which the fins are rotationally symmetrically arranged is parallel to the main extension direction of the base body. The rotational symmetry axis about which the fins are rotationally symmetrically arranged is preferably arranged parallel offset with respect to the main extension direction of the base body.

So as to further enhance safety, it is provided that the endoscopic device comprises the tube. In particular, the tube is designed in a manner corresponding to the endoscope shaft, the kink protector and/or the quick-release coupling.

Furthermore, an endoscope comprising at least the endoscopic device is claimed. In this way, an endoscope having improved properties with respect to safety can be provided.

Furthermore, a method for installing and/or removing the endoscopic device is claimed. In this way, an installation and/or removal process can be safely achieved.

Furthermore, a method for producing the endoscopic device is claimed. In this way, a safe endoscopic device can be provided. In particular, it can be avoided that individual components of the endoscopic device, such as the fin of the kink protector, can detach and jeopardize a secure connection.

The endoscopic device according to the invention and/or the method according to the invention shall not be limited to the above-described application and embodiment. In particular, the endoscopic device according to the invention and/or the method according to the invention can comprise a number of individual elements, components and units as well as method steps that deviates from the number described herein to fulfill an operating principle described herein. Moreover, in terms of the value ranges provided in the present disclosure, values that are within the described limits shall also be considered to be disclosed and arbitrarily usable.

In particular, it is pointed out that all features and properties described with respect to the device, but also procedures, can be applied mutatis mutandis and used within the meaning of the invention, and are considered to have been disclosed. The same also applies vice versa. This means that structural features, that is features according to device, described with respect to the method can also be taken into consideration, claimed and likewise considered to have been disclosed within the scope of the device claims.

If a particular component is present in more than one instance, only one is denoted by a reference numeral in the figures and in the description. The description of this instance can be applied accordingly to the other instances of the component.

BRIEF DESCRIPTION OF THE DRAWINGS

Further advantages will be apparent from the following description of the drawings. The drawings show one exemplary embodiment of the invention. The drawings, description and claims contain numerous features in combination. A person skilled in the art will advantageously also consider these features individually and combine them into useful further combinations.

In the drawings.

DESCRIPTION OF THE EMBODIMENTS

Figure 1:
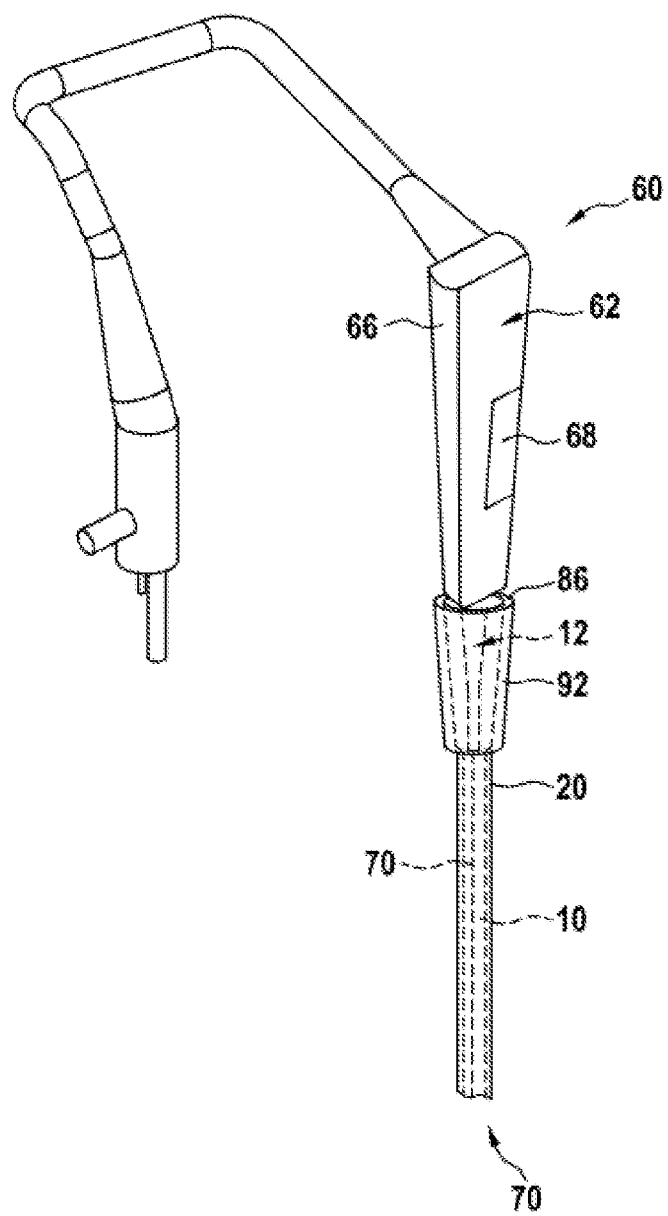
FIG. 1 shows a schematic illustration of an endoscope comprising an endoscopic device in a perspective view.
Figure 2:
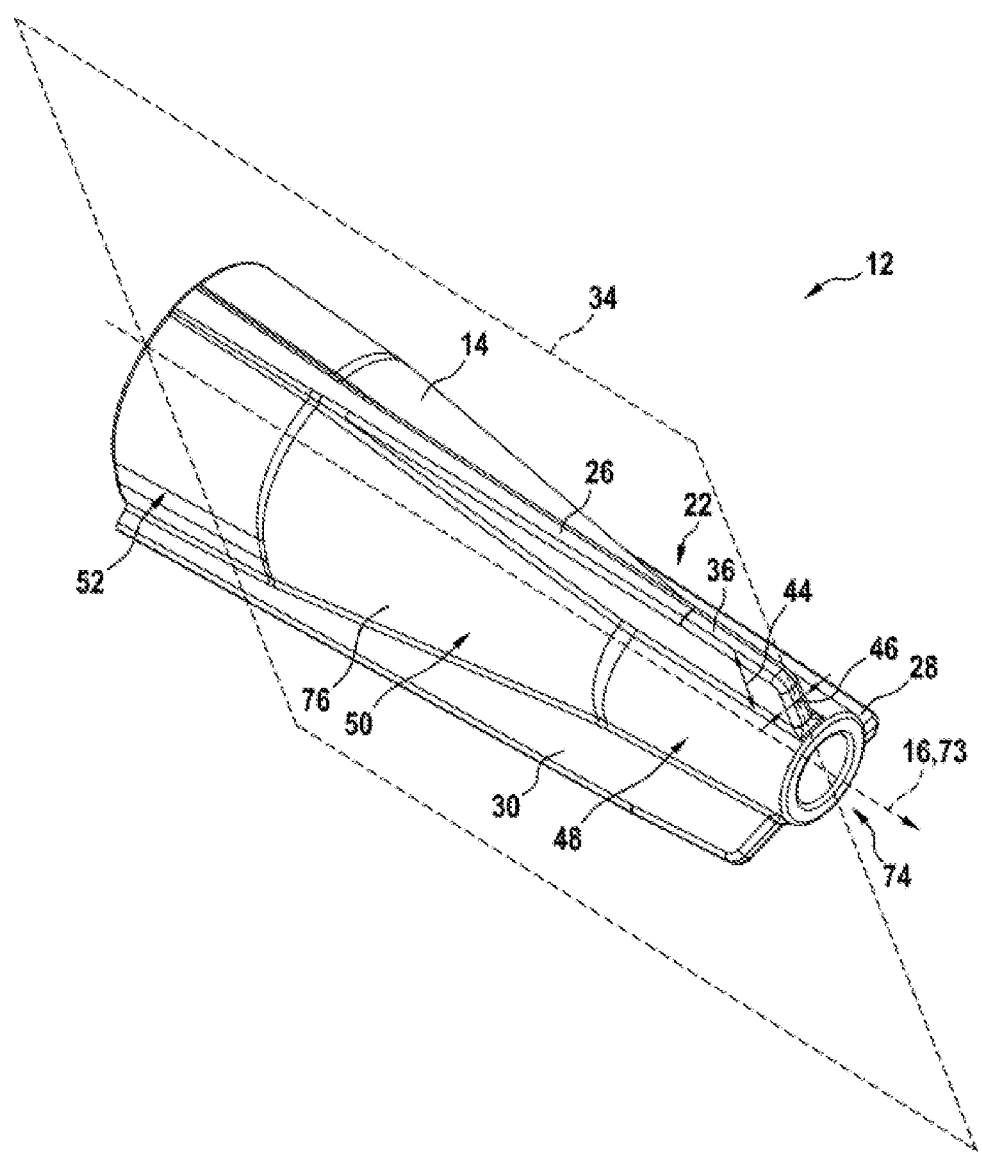
FIG. 2 shows a schematic illustration of a portion of the endoscopic device comprising a kink protector in a perspective view.

FIG. 1 shows a schematic illustration of an endoscope 60 comprising an endoscopic device in a perspective view. In the present case, the endoscopic device completely forms the endoscope 60. As an alternative, the endoscopic device could also only be a component part, an assembly of the endoscope 60 or the like.

The endoscopic device comprises a handle 62. The handle 62 comprises at least one grip 64. The handle 62 comprises a housing 66. The housing 66 is used to arrange further components of the endoscopic device. For example, a deflection mechanism for deflecting the endoscope shaft 10 is arranged in the housing 66. The handle 62 comprises an operating element 68. The operating element 68 is configured to operate a deflection of an endoscope shaft 10. The operating element 68 is operatively connected to the deflection mechanism.

The endoscopic device comprises the endoscope shaft 10. The endoscope shaft 10 has a flexible design. The endoscope shaft 10 is furthermore deflectable at least in sections. The endoscope shaft 10 is deflectable by way of the deflection mechanism. The endoscope shaft 10 is operatively connected to the operating element 68 by way of the deflection mechanism.

The endoscopic device comprises a tube 20. The tube 20 is a breathing tube or an endotracheal tube. The tube 20 is configured to be inserted into a trachea. The tube 20 includes a channel 70, which is configured to accommodate the endoscope shaft 10. The endoscope shaft 10 can be inserted at least partially into the tube 20. The tube 20 comprises a proximal end section 92. The proximal end section 92 is designed as a hollow cylinder. The proximal end section 92 of the tube 20 is configured to accommodate the kink protector 12.

The endoscopic device comprises at least one kink protector 12. The kink protector 12 is associated with the endoscope shaft 10. The kink protector 12 is configured to avoid sharp twisting of the endoscope shaft 10 and, in particular, damage associated therewith.

Figure 6:
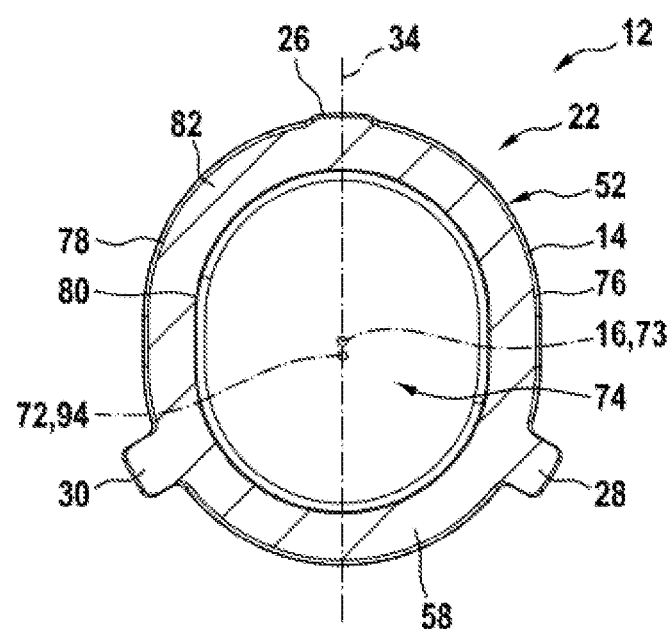
FIG. 6 shows a schematic illustration of the kink protector in a sectional view.
Figure 7:
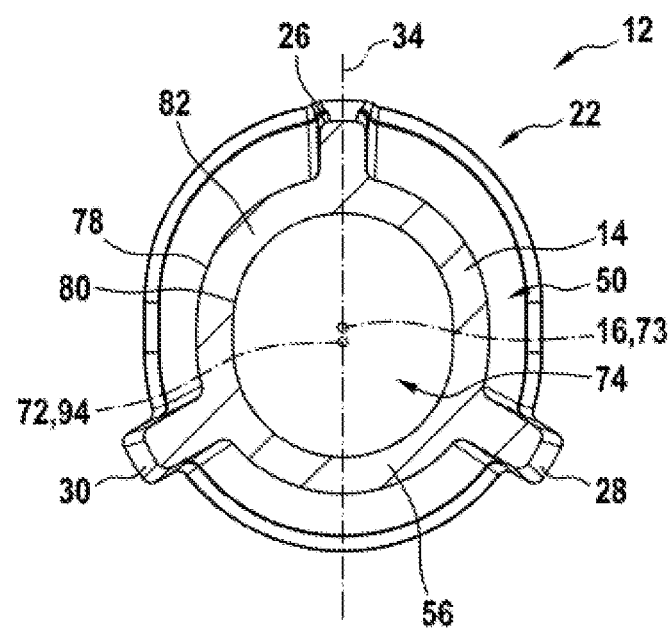
FIG. 7 shows a schematic illustration of the kink protector in a further sectional view.
Figure 8:
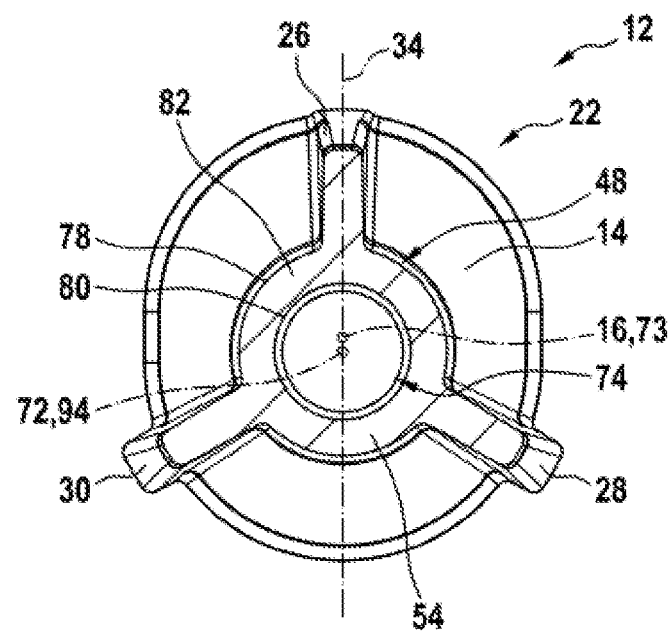
FIG. 8 shows a schematic illustration of the kink protector in an additional sectional view.

FIGS. 2 to 5 show schematic illustrations of the kink protector 12 in different perspective views. Furthermore, FIGS. 6 to 8 show schematic illustrations of the kink protector 12 in different sectional views.

The kink protector 12 comprises a base body 14. The base body 14 is free of rotational symmetry. The base body 14 has a main extension direction 16. The base body 14 has a main extension 18 along the main extension direction 16.

The base body 14 furthermore includes a recess 74. The recess 74 is configured to accommodate the endoscope shaft 10. A smallest inside diameter of the recess 74 corresponds to at least a largest outside diameter of the endoscope shaft 10.

The base body 14 comprises a jacket 76. The jacket 76 extends across the main extension 18 of the base body 14. The jacket 76 has an outer surface 78. The jacket 76 furthermore has an inner surface 80. The jacket 76 comprises a wall 82. The wall 82 is delimited by the inner surface 80 and the outer surface 78. The inner surface 80 delimits the recess 74. The wall 82 has a wall thickness. The thickness of the wall 80 is substantially constant along a main extension 18 of the base body 14.

The base body 14 has an at least partially elastic design. In the present case, the base body 14 is, at least to a large degree, designed in one piece. The base body 14 has a Shore hardness value of at least 40. The base body 14 furthermore has a Shore hardness value of no more than 80. In the present case, the base body 14 has a Shore hardness value of at least essentially 62.

The base body 14 is made at least partially of a medical plastic material. In the present case, the base body is, at least to a large degree, made of a medical plastic material. The medical plastic material is designed to withstand autoclaving processes. The plastic material is a thermoplastic elastomer. In the present case, the thermoplastic elastomer is known under the trade name Mediprene.

The base body 14 comprises at least one cylindrical section 48 (see FIG. 8). The cylindrical section 48 is a distal section of the base body 14. The recess 74 extends at least through the cylindrical section 48. The cylindrical section 48 has an outside diameter. The cylindrical section 48 furthermore has an inside diameter. The inside diameter corresponds to an outside diameter of the endoscope shaft 10. The cylindrical section has a rotational symmetry axis 72. The main extension direction 16 of the base body is at least parallel offset with respect to the rotational symmetry axis 72.

In addition, the base body 14 comprises at least one further cylindrical section 52. The further cylindrical section 52 is a proximal section of the base body 14. The recess 74 extends through the further cylindrical section 52. In the region of the cylindrical section 52, the base body 14 has a circular ring-shaped cross-section 54 (see FIG. 8).

The further cylindrical section 52 has a further outside diameter. The further outside diameter of the cylindrical section 52 is larger than the outside diameter of the cylindrical section 48. The cylindrical section 52 furthermore has a further inside diameter. The further inside diameter corresponds at least substantially to an outside diameter of the handle 62. The further inside diameter of the further cylindrical section 52 is larger than the inside diameter of the cylindrical section 48. The further inside diameter of the further cylindrical section 52 is moreover larger than the outside diameter of the cylindrical section 48. In the region of the further cylindrical section 52, the base body 14 has an oval ring-shaped cross-section 58 (see FIG. 6). The further cylindrical section 52 has a rotational symmetry axis 73. The main extension direction 16 of the base body is identical to the rotational symmetry axis 73.

The base body furthermore comprises at least one conical section 50. The conical section 50 is a central section of the base body 14. The recess 74 extends through the conical section 50. The conical section 50 is arranged between the cylindrical section 48 and the further cylindrical section 52. The conical section 50 connects the cylindrical section 48 and the further cylindrical section 52 to one another. The conical section 50 has an outside diameter. The outside diameter of the conical section increases along a main extension direction of the base body from the outside diameter of the cylindrical section 48 toward the further outer radius of the further cylindrical section 52. The conical section 50 has an inner radius. The inner radius of the conical section 50 increases from the inner radius of the cylindrical section 48 toward the further inner radius of the further cylindrical section 48. The increase in the diameter takes place continuously in the present case. As an alternative, the increase in the diameter could also take place incrementally. In the region of the conical section 50, the base body 14 has an oval ring-shaped cross-section 56 (see FIG. 6).

Figure 4:
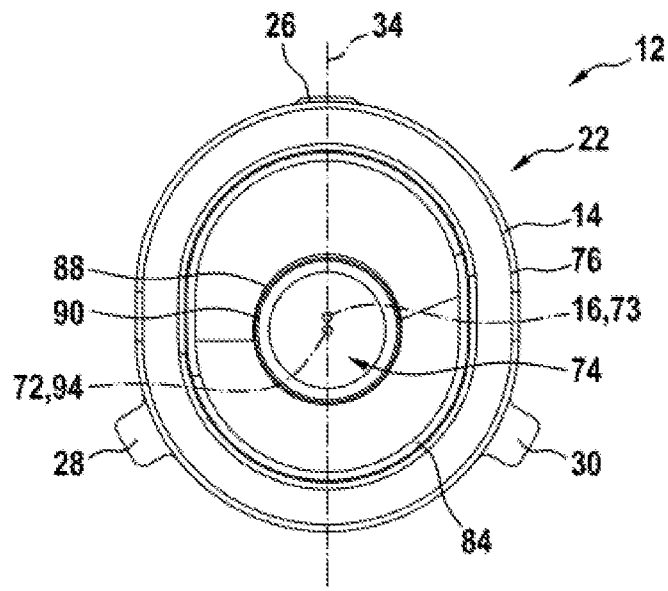
FIG. 4 shows a schematic illustration of the kink protector in a rear view.
Figure 5:
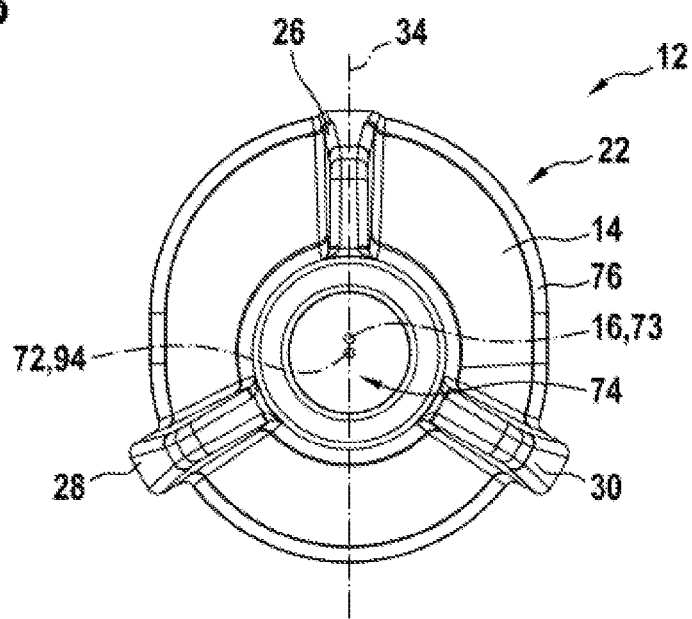
FIG. 5 shows a schematic illustration of the kink protector in a front view.

The kink protector 12 comprises at least one connecting element 84 for a connection of the kink protector 12 to the handle 62 (see FIG. 4). The connecting element 84 is arranged at the base body 14. The connecting element 84 is arranged in the section 52. The connecting element 84 is arranged at the inner surface 80. In the present case, the connecting element 84 is designed as an annular lip. The connecting element 84 is designed in one piece with the base body 14. When the kink protector 12 has been pushed onto the endoscope shaft 10 up to the handle 62, the connecting element 84 establishes a connection between the kink protector 12 and the handle 62. The handle 62 comprises a connecting element 86 that corresponds to the connecting element 84 and, during a connection, latchingly engages the connecting element 84.

The kink protector 12 comprises at least one locking element 88 so as to lock the kink protector 12 to the endoscope shaft 10 (see FIG. 4). In the present case, the kink protector comprises at least one further locking element 90, which is arranged at a distance from the locking element 88. Only one locking element 88 is described in more detail hereafter. The description can be applied to the further locking element 90. The locking element 88 is arranged at the base body 14. The locking element 88 is arranged in the section 48. The locking element 88 is arranged at the inner surface 80. In the present case, the locking element 88 is designed as an annular lip. The locking element 88 is designed in one piece with the base body 14. When the kink protector 12 is pushed onto the endoscope shaft 10, the locking element 88 interlocks with the endoscope shaft 10.

For a detachable connection to the tube 20, the kink protector 12 comprises at least one quick-release coupling 22. The quick-release coupling 22 is configured for a form-locked and/or force-fit connection to the tube 20. The quick-release coupling 22 comprises at least one fin 26. The fin 26 is arranged so as to be situated substantially perpendicularly on the base body 14. The fin 26 is situated perpendicularly on the jacket 76 of the base body 14. The fin 26 is configured to bend laterally upon contact with the tube 20.

Figure 3:
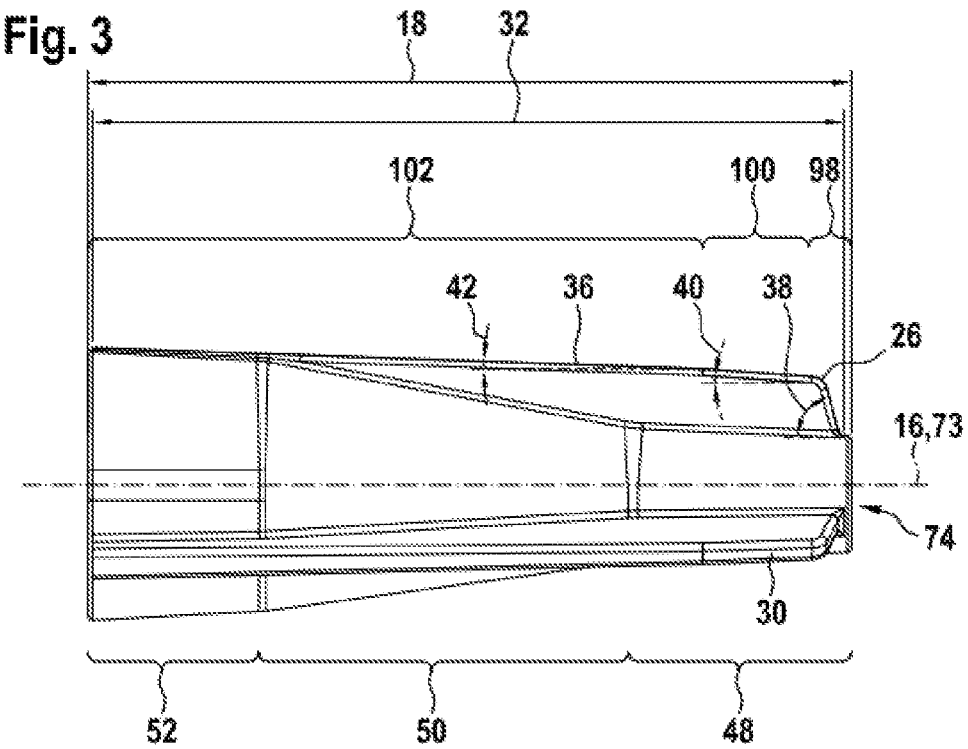
FIG. 3 shows a schematic illustration of the kink protector in a side view.

The fin 26 has an extension 32 along the main extension direction 16 of the base body 14, which extends at least across 50% of the main extension 18 of the base body 14 (see FIG. 3). In the present case, the extension 18 of the fin 26 even extends across at least 80% of the main extension 18 of the base body 14.

Moreover, a main extension plane 34 of the fin 26 is oriented at least substantially parallel to the main extension direction 16 of the base body 14. More precisely, the main extension direction 16 of the base body 14 is situated in the main extension plane 34 of the fin 26.

The fin 26 comprises at least one outside edge 36 facing away from the base body 14. An angle 38, 40, 42 of the outside edge 36 relative to the main extension direction 16 decreases along the main extension 18 of the base body 14, and more particularly in the proximal direction. In the present case, the angle 38, 40, 42 decreases incrementally. As an alternative, the angle 38, 40, 42 could also decrease continuously.

The fin 26 comprises at least one first section 98. The first section 98 extends within a region of the cylindrical section 48 of the base body 14. In the first section 98, the outside edge 36 has an angle 38 relative to the main extension direction 16 of no more than 80°. The fin 26 furthermore comprises a second section 100. The second section 100 extends in a region of the cylindrical section 48 of the base body 14. In the second section 100, the outside edge 36 of the fin 26 has an angle 40 relative to the main extension direction 16 of no more than 10°. The fin 26 furthermore comprises a third section 102. The third section 102 extends across a region of the cylindrical section 48, of the conical section 50, and of the cylindrical section 52 of the base body 14. In the third section 102, the outside edge 36 of the fin 26 has an angle 38, 40, 42 relative to the main extension direction 16 of no more than 5°. As seen in the proximal direction, the second section 100 is arranged behind the first section 98. As seen in the proximal direction, the third section 102 is arranged behind the second section 100. The second section 100 connects the first section 98 and the third section 102 to one another.

The fin 26 has a height 44 relative to the base body 14. The fin 26 furthermore has a thickness 46. The thickness 46 is measured perpendicularly to the main extension plane 34 of the fin 26. The height 44 of the fin 26 corresponds at least to twice a thickness 46 of the fin 26, and more particularly in the first section 98 of the fin 26. Due to different section of the base body 14 and of the fin 26, a relative height 44 of the fin 26 decreases as seen in the proximal direction, measured relative to the base body 14.

The fin 26 is at least partially made of an elastic material. The elastic material has a Shore hardness value of at least 40. The elastic material furthermore has a Shore hardness value of no more than 80. In the present case, the elastic material has a Shore hardness value of at least essentially 62. The material is a medical plastic material. The material is a thermoplastic elastomer. In the present case, the material is known under the trade name Mediprene.

In the present case, the fin 26 is designed in one piece with the base body 14. In the present case is, the fin 26 is made of the same material as the base body 14. The fin 26 and the base body 14 form an injection molded assembly. As an alternative, the fins 26, 28, 30 and the base body 14 could also be produced separately from one another. The fin 26 and the base body 14 could then be joined to one another. For example, the fin 26 and the base body 14 could be welded or adhesively bonded to one another. Furthermore, it is conceivable to produce the base body and the fin 26 by way of multi-component injection molding.

The quick-release coupling 22 comprises at least one further fin 28. The further fin 28 is designed to be at least substantially identical to the fin 26. In the present case, the quick-release coupling 22 comprises at least one additional fin 30. The additional fin 30 is designed to be at least substantially identical to the fin 26. Accordingly, the quick-release coupling 22 comprises a total of three fins 26, 28, 30. The quick-release coupling 22 could furthermore comprise a number of fins 26, 28, 30 deviating from that shown here, for example so as to vary a clamping force.

The fins 26, 28, 30 are arranged rotationally symmetrically with respect to one another at the base body 14. In the present case, the fins 26, 28, 30 are arranged at the base body 14 corresponding to a three-fold rotational symmetry. The degree of the rotational symmetry can be varied by way of the number of fins. A rotational symmetry axis 94 of the rotational symmetry of the fins 26, 28, 30 is different from the rotational symmetry axis 73. The rotational symmetry axis 94 is identical to the rotational symmetry axis 72. The rotational symmetry axis 94 of the fins 26, 28, 30 is parallel to the main extension direction 16 of the base body 14. The rotational symmetry axis 94 of the fins 26, 28, 30 is offset parallel with respect to the main extension direction 16 of the base body 14.

Given the fact that the base body 14 is free of rotational symmetry, and the fins 26, 28, 30 are arranged corresponding to a three-fold rotational symmetry, the kink protector 12 overall does not have rotational symmetry itself. The kink protector 12 has mirror symmetry. A mirror plane of the mirror symmetry of the kink protector 12 corresponds to the main extension plane 34 of the fin 26.

Figure 9:
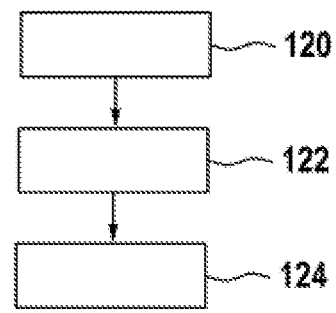
FIG. 9 shows a schematic flow chart of an exemplary method for producing the endoscopic device.

FIG. 9 shows a schematic flow chart of a method for producing the endoscopic device.

The method comprises at least one method step 120. In the method step 120, a shape is created which corresponds to a negative of the desired kink protector 12.

The method comprises at least one further method step 122. The material is liquefied in the further method step 122. The material is added to the mold. The material is cured in the mold. The kink protector 12 is formed.

The method comprises a further method step 124. The kink protector 12 is removed from the mold in the further method step 124. Thereafter, the kink protector 12 is ready for use.

Figure 10:
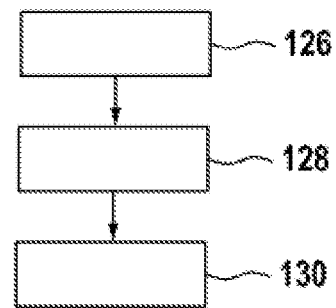
FIG. 10 shows a schematic flow chart of an exemplary method for installing and/or removing the endoscopic device.

FIG. 10 shows a schematic flow chart of an exemplary method for installing and/or removing the kink protector 12.

The method comprises at least one method step 126. The endoscope shaft 10 is inserted into the recess 74 of the kink protector 12 in the method step 126. The kink protector 12 is guided in the proximal direction along the endoscope shaft 10. The kink protector 12 is guided along the endoscope shaft 10 until the handle 62 is reached. The kink protector 12 is furthermore connected to the handle 62.

The method comprises at least one further method step 128. The tube 20 is guided onto the endoscope shaft 10 in the further method step 128. The tube 20 is guided onto the endoscope shaft 10 until the proximal end section of the tube 20 makes contact with the kink protector 12.

The method comprises at least one further method step 130. The tube 20 is connected to the kink protector 12 by way of the quick-release coupling 22 in the further method step 130. The proximal end section 92 of the tube 20 is guided over the fins 26, 28, 30 of the kink protector 12. In the process, the proximal end section 92 of the tube 20 pushes the fins 26, 28, 30 to the side, so that these deform laterally and become clamped inside the end section. The fins 26, 28, 30 clamp the tube 20 to the kink protector 12 from the inside.

Furthermore, the tube 22 can be removed by applying a force to the tube 20 in the distal direction which is greater than the clamping force of the fins 26, 28, 30 acting on the tube 20. As an alternative or in addition, the tube 20 can be rotated relative to the kink protector 12 so as to thereby laterally overcome static friction of the fins 26, 28, 30 and thus reduce a clamping force acting on the inside wall of the tube.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

| | |
|---|---|
| 10 | endoscope shaft |
| 12 | kink protector |
| 14 | base body |
| 16 | main extension direction |
| 18 | main extension |
| 20 | tube |
| 22 | quick-release coupling |
| 26 | fin |
| 28 | fin |
| 30 | fin |
| 32 | extension |
| 34 | main extension plane |
| 36 | outside edge |
| 38 | angle |
| 40 | angle |
| 42 | angle |
| 44 | height |
| 46 | thickness |
| 48 | section |
| 50 | section |
| 52 | section |
| 54 | cross-section |
| 56 | cross-section |
| 58 | cross-section |
| 60 | endoscope |
| 62 | handle |
| 64 | grip |
| 66 | housing |
| 68 | operating element |
| 70 | channel |
| 72 | rotational symmetry axis |
| 73 | rotational symmetry axis |
| 74 | recess |
| 76 | jacket |
| 78 | outer surface |
| 80 | inner surface |
| 82 | wall |
| 84 | connecting element |
| 86 | corresponding connecting element |
| 88 | locking element |
| 90 | locking element |
| 92 | end section |
| 94 | rotational symmetry axis |
| 98 | section |
| 100 | section |
| 102 | section |
| 120 | method step |
| 122 | method step |
| 124 | method step |
| 126 | method step |
| 128 | method step |
| 130 | method step |

The invention claimed is:

1. An endoscope, comprising:
at least one flexible endoscope shaft; and
at least one kink protector, which is configured to receive the endoscope shaft therethrough and comprises at least one base body that is at least partially frustoconically shaped, the at least one base body having a main extension direction and a main extension along the main extension direction, and the kink protector comprises at least one quick-release coupling, which is configured for a selective connection to a tube and includes at least one fin situated at least substantially perpendicularly to and longitudinally along the base body, wherein the fin has an extension extending along the main extension direction of the base body at least across 50% of the main extension of the base body, wherein the fin bends laterally upon contact with the tube and wherein the fin also increases in height from a proximal end toward a distal end.

2. The endoscope according to claim 1, wherein a main extension plane of the fin is oriented at least substantially parallel to the main extension direction of the base body.

3. The endoscope according to claim 1, wherein the fin comprises at least one outside edge facing away from the base body, at least one angle of the outside edge relative to the main extension direction of the base body decreasing along the main extension thereof.

4. The endoscope according to claim 1, wherein the fin is designed to be at least partially elastic.

5. The endoscope according to claim 1, wherein the fin is made at least partially of a material having a Shore hardness value of at least 40 and/or of no more than 80.

6. The endoscope according to claim 1, wherein the fin is made at least partially of a material which is a thermoplastic elastomer.

7. The endoscope according to claim 1, wherein the fin has a height in sections, at least measured relative to the base body, which corresponds at least to twice a thickness of the fin.

8. The endoscope according to claim 1, wherein the base body comprises the at least one frustoconical section and at least one cylindrical section.

9. The endoscope according to claim 1, wherein the base body, cut perpendicularly to the main extension direction thereof, has a cross-section deviating from a circular ring shape at least in sections.

10. The endoscope according to claim 1, wherein the fin is one piece with the base body.

11. The endoscope according to claim 1, wherein the quick-release coupling comprises at least one further fin, which is designed substantially identically to the fin.

12. The endoscope according to claim 11, wherein the fin and the further fin are arranged rotationally symmetrically relative to one another about a rotational symmetry axis at the base body.

13. The endoscope according to claim 12, wherein a rotational symmetry axis of the fins is different from the main extension direction of the base body.

14. The endoscope according to claim 1, wherein the tube is fitted over the at least one kink protector and the endoscopic shaft.

15. An endoscope anti-kink adapter device comprising:
a body having a first proximal end and a second distal end, and a hole therethrough extending from the first proximal end to the second distal end that is adapted to receive at least one flexible endoscope shaft, the body having a portion that is frustoconically shaped; and
a plurality of fins located longitudinally along the body, the fins tapering inward towards the second distal end with the fins also increasing in height from the first proximal end toward the second distal end, the fins configured to deform laterally to accommodate a plurality of tube sizes placed on the body from the second distal end,
wherein the body further includes at least one cylindrically shaped portion at either the first proximal end or the second distal end that abuts the frustoconically shaped portion.

16. The device of claim 15, wherein the body is a thermoplastic elastomer, and there is a cylindrically shaped portion on both the first proximal end and the second distal end of the body.

17. The device of claim 16, wherein the cylindrically shaped portion at the first proximal end of the body is adapted to engage a handle of an endoscope.

18. The device of claim 15, wherein the fins are rotationally symmetric with respect to one another.

19. The device of claim 15, further comprising a lock at the first proximal end that engages a handle of an endoscope.

20. A endoscope with an anti-kink adapter device comprising:
a flexible endoscopic shaft;
a body having a first proximal end and a second distal end, and a hole therethrough extending from the first proximal end to the second distal end that is adapted to receive the flexible endoscope shaft, the body having a portion that is frustoconically shaped, the first proximal end of the body being attached to a handle of the endoscope; and
a plurality of fins located longitudinally along the body, the fins tapering inward towards the second distal end with the fins also increasing in height from the body from the first proximal end toward the second distal end, the fins configured to deform laterally to accommodate a plurality of endotracheal tube sizes placed on the body from the second distal end,
wherein the body further includes at least one cylindrically shaped portion at either the first proximal end or the second distal end that abuts the frustoconically shaped portion.

21. An endoscope, comprising:
at least one flexible endoscope shaft; and
at least one kink protector, which is configured to receive the endoscope shaft therethrough and comprises at least one base body that includes at least two partially frustoconically shaped portions, the at least one base body having a main extension direction and a main extension along the main extension direction, and the kink protector comprises at least one quick-release coupling, which is configured for a selective connection to a tube and includes at least one fin situated at least substantially perpendicularly to and longitudinally along the base body, wherein the fin extends along the at least two partially frustoconically shaped portions and has an extension extending along the main extension direction of the base body at least across 50% of the main extension of the base body, and wherein the fin bends laterally upon contact with the tube.

* * * * *